United States Patent [19]

Nath et al.

[11] Patent Number: 4,539,987
[45] Date of Patent: Sep. 10, 1985

[54] APPARATUS FOR COAGULATION BY HEAT RADIATION

[76] Inventors: Günther Nath, Dr. Max-Strasse 76, Grünwld, Fed. Rep. of Germany, D-8022; Albert Kreitmair, Deisenhofenerstr.79d; Vincent Jaeger, Buchnerstrasse 9, both of München, Fed. Rep. of Germany, D-8000

[21] Appl. No.: 617,140

[22] Filed: Jun. 4, 1984

Related U.S. Application Data

[63] Continuation of Ser. No. 237,669, Feb. 24, 1981, abandoned.

[30] Foreign Application Priority Data

Feb. 27, 1980 [DE] Fed. Rep. of Germany ....... 3007388

[51] Int. Cl.³ ............................................ A61B 17/38
[52] U.S. Cl. ................................. 128/303.1; 128/397; 128/398; 219/85 BA; 219/354
[58] Field of Search ..................... 128/303.1, 395–398; 219/354, 85 BA

[56] References Cited

U.S. PATENT DOCUMENTS 4,233,493 11/1980 Nath .............................. 128/303.1 X

FOREIGN PATENT DOCUMENTS 2717421 11/1978 Fed. Rep. of Germany ... 128/303.1

Primary Examiner—Lee S. Cohen
Attorney, Agent, or Firm—Brumbaugh, Graves, Donohue & Raymond

[57] ABSTRACT

In a radiation coagulator having an electric incandescent lamp, in particular a tungsten-halogen low-voltage lamp, as radiation source, and a tissue contact element of a crystalline dielectric material transmissive to the radiation, forming a contact surface to be pressed against living body tissue, the temperature conductivity (reciprocal of the temperature resistance), the heat capacity of the contact element, possibly in combination with a heat sink attached thereto, is so great that the heat generated in the tissue in contact with said surface is derived in substantial measure from the tissue contact element. This prevents an over-rapid and over-intense temperature rise at the surface of the tissue, leading to a considerable improvement in coagulability, especially for severe parenchymatous hemorrhages, and to lessened adhesion to the contact surface, and permitting a gentle coagulation, extending into depth if desired. Besides, the tissue contact element is free from any exposed sharp edges that might cut into the tissue and injure it or cause an excessive concentration of radiation. A preferred material for the tissue contact element is monocrystalline sapphire; other suitable materials are beryllium or magnesium oxide, or monocrystalline quartz.

26 Claims, 9 Drawing Figures

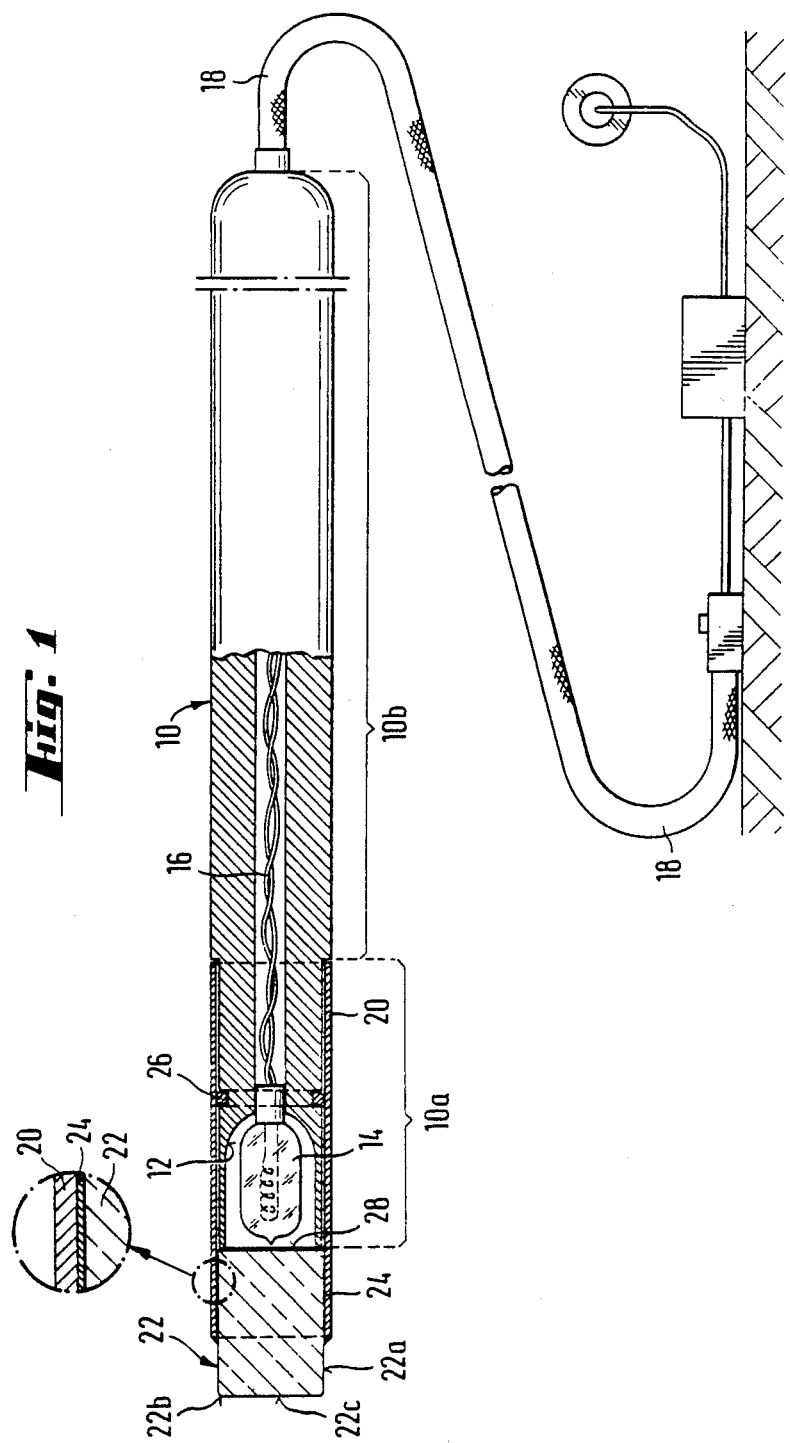

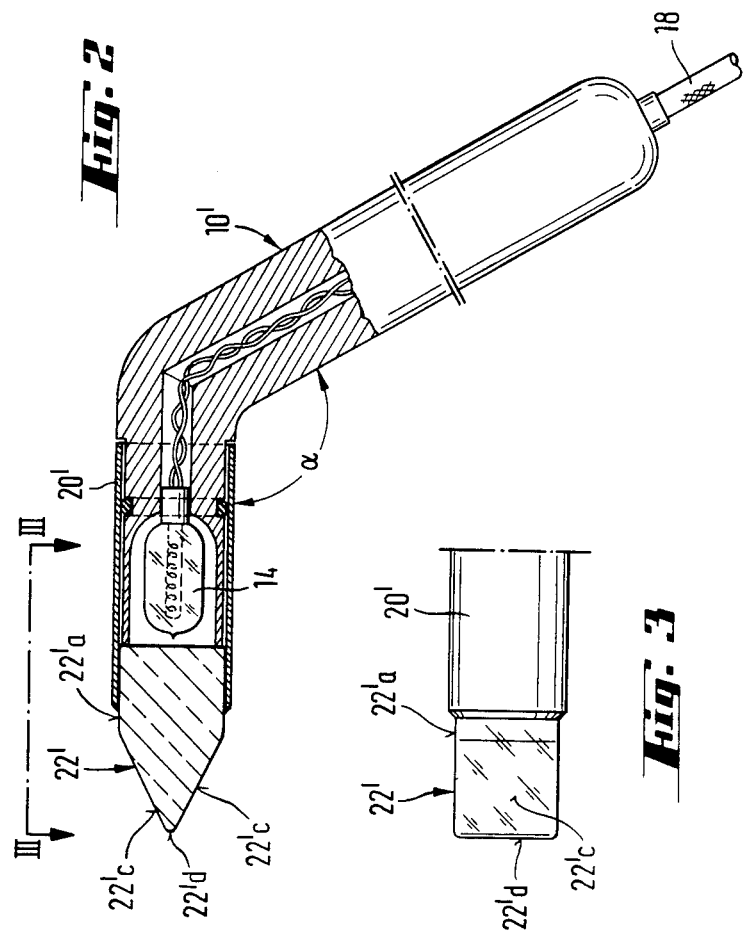

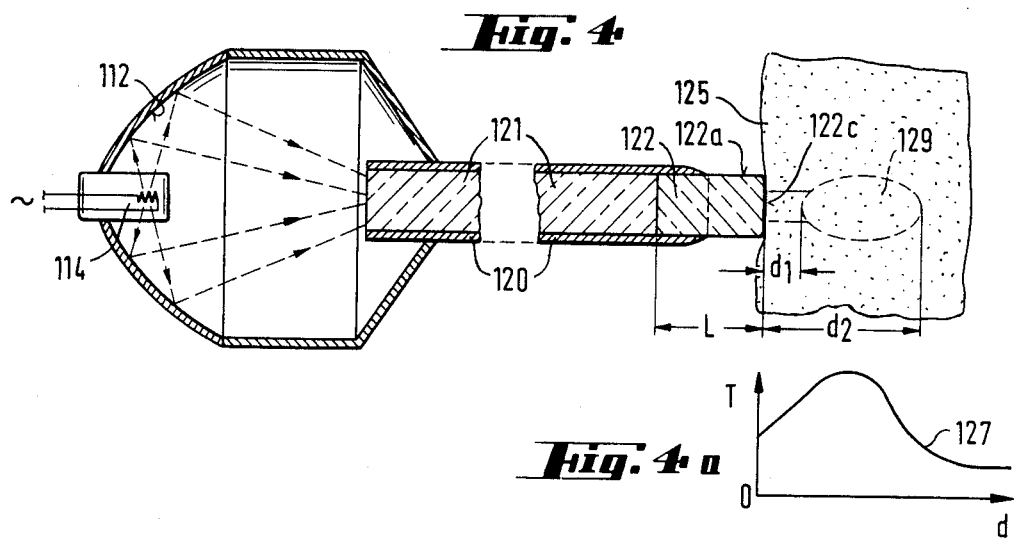
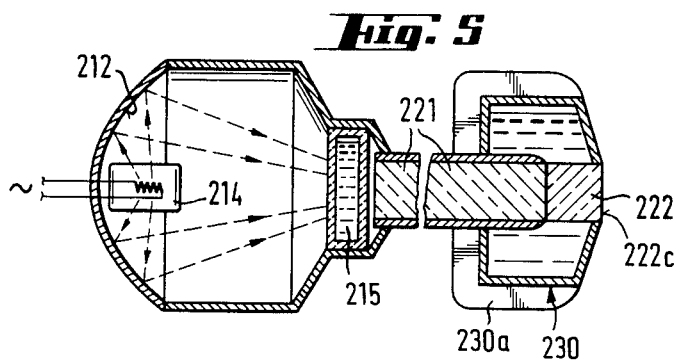
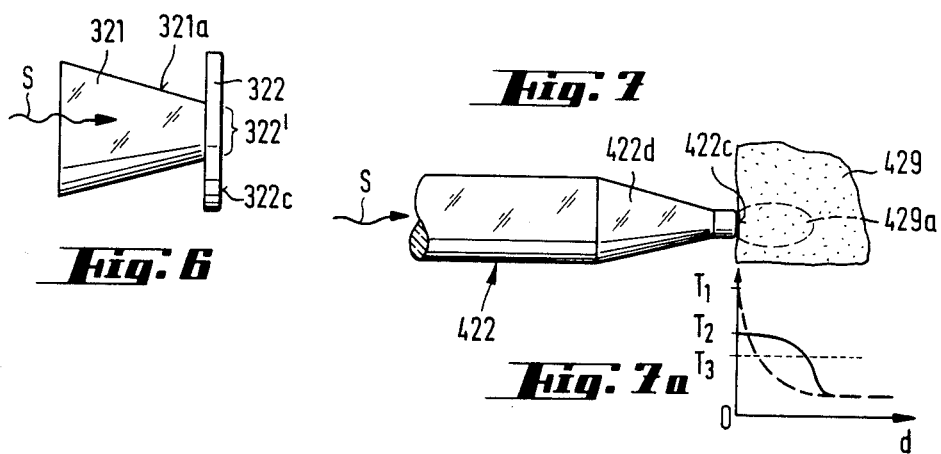

APPARATUS FOR COAGULATION BY HEAT RADIATION

This application is a continuation of application Ser. No. 237,669, filed Feb. 24, 1981, now abandoned.

BACKGROUND OF THE INVENTION

The present invention relates to a radiation coagulator having an incandescent electric filament as source of radiation and a radiation output means comprising a tissue contact element of a crystalline dielectric material transparent to the radiation, traversed by the thermal radiation and forming a contact surface to be held against living body tissue.

Such a coagulator is disclosed in German Letters of Disclosure No. 2,717,421. It is highly serviceable for arresting moderate hemorrhages. It is desirable, however, to be able to arrest more severe hemorrhages and still further reduce adhesion of the contact element to the tissue. Further, the appliance should also be suitable for arresting hemorrhages in very soft and sensitive tissue, such as liver tissue. For certain purposes, moreover, for example destruction of blood vessels passing beneath the surface of the skin, it is desirable to keep the evolution of heat in the skin adjacent to the contact surface and in the immediately adjoining layer of tissue comparatively low, so that coagulation will become effective only at a certain distance from the surface of the skin.

SUMMARY OF THE INVENTION

The object of the present invention accordingly is to develop a radiation coagulator of the kind initially mentioned in such a way that any excessive evolution of heat at the surface of the tissue in contact with the element pressed against it will be avoided and adhesion of the tissue to the contact surface will be further reduced.

This object is accomplished, in a radiation coagulator having an incandescent electric filament as source of heat radiation and a radiation output means comprising a tissue contact element of a crystalline dielectric material transparent to the radiation, to be traversed by the radiation and form a contact surface pressed against the body tissue, in that, according to the invention, the radiation output density at the tissue contact surface is at most 150 W/cm$^2$, preferably at most 100 W/cm$^2$, and in that the thickness of the tissue contact element, reckoned in perpendicular direction from the tissue contact surface, is generally at least 4 mm.

The heat withdrawal capacity of the radiation output means including the tissue contact element is preferably so great that upon penetration of the coagulating radiation, the tissue contact element is heated at the contact surface by at most 50 degrees within 2 seconds while the surface is in contact with typical living body tissue, such as muscle tissue. In particular, the temperature rise during the time of treatment should not be so great that the tissue adjacent to the contact surface will dry out completely, and especially not so great as to char the tissue.

Owing to the fact that the tissue contact element as dimensioned according to the invention has a high heat capacity relative to the radiation output density, a substantially slower and more uniform temperature rise occurs at the contact surface during the process of coagulation than in known radiation coagulators, so that a deeper zone of coagulation is obtained, with no carbonized surface layer to impede entry of the radiation, and hence a surprising improvement in hemostasis and lessened adhesion of the tissue to the contact surface. If the tissue contact element, as is preferably the case, is free from exposed sharp, cutting edges, even sensitive tissue, such as liver tissue, can be coagulated without fear of injuries (cuts). Furthermore, with suitable choice of the wavelength interval of the radiation and the output density prevailing at the tissue contact surface, it can be ensured that there will be no excessive alteration of the tissue surface with which the element is placed in contact, and that instead the coagulation will become effective only from a certain depth within the tissue.

This high capacity to take up heat rapidly is advantageously achieved through a high heat capacity and a high thermal conductivity of the tissue contact element. Alternatively, however, means may be provided to withdraw heat from the tissue contact surface, in other words some sort of cooling element or cooling means. That is, the tissue contact element may advantageously act as a fast "heat sink"; this is to say that it rapidly conducts heat away from the region of tissue adjacent to the contact surface, so that the tissue in contact is not heated too intensely. Rounding of the edges of the tissue contact element avoids injuries (cuts) and undue concentration of radiation at the edges, which might lead to excessive tissue adhesion.

The material of the contact element is to have a temperature resistance, at 20° C., of $$R_T = c\rho/\lambda \leq 20 \text{ sec. cm}^{-2}$$

where
  c = specific heat [Jg$^{-1}$K$^{-1}$],
  $\rho$ = density [g cm$^{-3}$],
  $\lambda$ = heat conductivity [J cm$^{-1}$ sec.$^{-1}$K$^{-1}$].
Preferably, $R_T \leq 10$ sec. cm$^{-2}$. For sapphire, the temperature resistance is about 7 sec. cm$^{-2}$ at 20° C.

By virtue of the aforementioned dimensioning of the mean thickness $\bar{d}$ of the contact element, a preferred specific heat capacity $\Gamma$ of the contact element (heat capacity of the contact element per unit area of the contact surface) of $$\Gamma = c \cdot \rho \cdot \bar{d} > 0.4 J \text{ cm}^{-2} K^{-1}$$

is obtained.

The tissue contact element of course consists of a material transmissive, in other words preferably transparent but at least translucent, to the incoherent radiation effecting the coagulation. If a shielding problem exists, the lower limit of the radiation interval may advantageously be about 0.6 to 0.7$\mu$.

Especially suitable materials for the tissue contact element are, in the order of mention, sapphire monocrystals, MgO, BeO, monocrystalline quartz, and possibly als TiO$_2$, SrTiO$_3$ and ZrO$_2$.

BRIEF DESCRIPTION OF THE DRAWINGS

In the following, the invention will be further illustrated by examples of embodiments with reference to the drawing; at the same time, mention will be made of still other advantages and refinements of the radiation coagulator according to the invention.

In the drawing,

FIG. 1 shows an axial section of a first preferred embodiment of the invention;

FIG. 2 shows a side view, in partial section, of a modification of the embodiment of FIG. 1;

FIG. 3 shows a top view of the radiation exit means of the coagulator according to FIG. 2;

FIGS. 4 and 5 show two additional embodiments of the invention in axial section;

FIG. 4a shows a related temperature distribution curve;

FIGS. 6 and 7 show side views of additional embodiments of radiation exit meanss for radiation coagulators according to the invention;

FIG. 7a shows a related temperature distribution curve.

DESCRIPTION OF EXEMPLARY EMBODIMENTS

The substantially cylindrical, rod-shaped radiation coagulator represented in axial section in FIG. 1 is at this time the preferred embodiment of the present invention. It comprises a member serving as a handle, in the form of a thick-walled tube 10, preferably of stainless steel. In the anterior end of the tube 10, by machining or the like, an ellipsoidal reflector 12 is formed, its surface highly polished and preferably plated with gold. In the reflector 12 there is an incandescent lamp 14 to serve as source of heat radiation, in particular a tungsten-halogen low-voltage lamp, closely embraced by the reflector 12. The clearance between the lamp envelope and the reflector is preferably at most 5 mm, preferably about 2 mm. The incandescent lamp 14 is connected by way of a connecting line 16 passing through the central hole of the tube 10 to a connecting line 18 set, preferably liquid- and vapor-tight, in the rounded posterior end of the tube 10. In the embodiment illustrated in FIG. 1, the connecting line 18 leads to the tube 10 from a current supply circuit for the filament.

The tube 10 has a somewhat smaller diameter in an anterior portion 10a, so that a thin-walled tube 20 may be slipped on, consisting for example of stainless steel and so dimensioned that its exterior is substantially flush with the exterior of the posterior portion 10b of the tube 10. In the anterior end of the tube 20 is inserted a tissue contact element 22 consisting of a cylindrical piece of sapphire monocrystal. The tissue contact element 22 is bonded to the tube 20 by means of a layer 24 of silicone adhesive resistant to elevated temperatures. The cylindrical exterior surface 22a of the tissue contact element 22 is highly polished, so that the tissue contact element can act as a short optical guide. The anterior annular edge 22b of the tissue contact element is rounded (the radius of the rounding may for example be 0.5 mm), so that there is no danger of damage to sensitive tissue by the edge of the tissue contact surface 22c formed by the face of the element.

The silicone adhesive layer 24 will not interfere with the optical guide function, its refractive index being below that of sapphire.

Portion 10a of tube 10 is provided with an annular groove accepting an O-ring seal 26. This O-ring seal, the silicone adhesive layer 24 and the seal where the cable 18 enters the posterior end of tube 10 ensure that the coagulator represented in FIG. 1 can be steam autoclaved without danger of entry of steam into the interior and consequently of damage to the reflector 12 or other internal parts of the coagulator.

On the radiation entrance surface of the tissue contact element 22 facing the incandescent lamp 14, a dielectric thin-layer filter 28 may be applied by vapor deposition, limiting the lower bound of the spectral interval transmitted to, for example, 600 nm so as to reduce the glare effect of the emerging radiation. Alternatively, or in addition, the sapphire constituting the tissue contact element 22 may be doped in known manner with chromium ions, so that it assumes a red color, likewise reducing the glare effect. Furthermore, in a radiation coagulator of the kind represented in FIG. 1, the portion of tissue contact element 22 protruding from the tube 20 will be made as short as possible, in particular shorter than 10 mm, preferably shorter than 3 mm, in particular about 1 mm.

When using an incandescent lamp 14 with a rating of 250 W, the anterior end of reflector 12 and the tissue contact element 22 are preferably about 16 mm in diameter. With a 12-mm or 25-mm diameter of the cylindrical tissue contact element, it is expedient to employ incandescent lamps with ratings of 150 or 400 W, respectively.

The temperature distribution occurring in the course of a coagulation corresponds to that described below with reference to FIG. 7.

The coagulator represented in FIG. 2 differs from that of FIG. 1 in two respects. Firstly, the tube 10' is bent, the angle α of the bend being preferably between about 90° and 150°. Secondly, the tissue contact element 22' has a wedge-like tapering end to facilitate coagulation in fissures of tissue, for example in accidental injuries to the liver. However, all exposed edges of the wedge-shaped tissue contact element 22' are rounded, so that they will not act as cutting edges and cause injuries.

The tube 20' may be textured on the outside (not shown) to facilitate rotating it in order to change the orientation of the straight anterior edge 22'd of the wedge relative to the tube 10'. Thus, the tissue contact element 22' here has two tissue contact surfaces 22'c. The cylindrical portions 22'a of the lateral surfaces are again highly polished. The wedge angle of the tissue contact element 22' may for example be between 40° and 90°; it is preferably about 60°. It must not of course be so small that emergence of the radiation will be hindered by total reflection.

In the coagulators according to FIGS. 1 and 2, the lamp 14 is preferably arranged at a close distance from the light entrance surface of the tissue contact element, but without touching it. The distance from the envelope of the lamp 14 to the light entrance surface may for example be 1 to 2 mm, and preferably is no more than 10 mm.

The embodiment illustrated by way of example with reference to FIG. 2 may be modified so that instead of a bent tube 10', a rod-like member is used comprising a flexible wedge, so that the angle α may be adjusted at will. The flexible portion may for example consist of a length of corrugated tubing.

A further modification of the embodiments above described by way of example consists in the use of a tissue contact element in the form of a cylindrical rod one face of which, acting as light entrance surface, is perpendicular to the axis, while the other face, serving as tissue contact surface, is oblique to the axis. Again, the angle this oblique surface makes with the axis must not be so great that exit of radiation is obstructed by total reflection. As before, all exposed edges are rounded so that they cannot cause injury. Alternatively, the contact element may have the shape of an oblique cylinder, i.e. a plate with parallel radiation entrance and exit surfaces oblique to the mean direction of radiation.

Finally, a tissue contact element in the form of a prism with two faces at an angle of 90° to each other may be used, one acting as light entrance surface and the other as tissue contact surface, with an oblique surface at which the light having entered through the entrance surface is reflected towards the tissue contact surface.

The radiation coagulator represented in FIG. 4 may in principle be constructed as described in German Letters of Disclosure No. 2,717,421 with reference to FIG. 1 thereof. It contains a heat radiation source in the form of a tungsten-halogen low-voltage lamp 114 having a reflector 112 in the form of a hollow mirror of aluminum. Instead of the aluminum reflector, use may alternatively be made of a reflector with a reflective layer of gold, or a dielectric thin-layer reflector selectively reflecting in the band of wavelengths between about 0.6 and 1.4μ.

The coagulator according to FIG. 4 further contains a rigid optical guide 121 in the form of a quartz rod of circular cross section, enclosed by a thin metal tube 120. The reflector 112 reflects the heat radiation of the incandescent lamp 114 into a light input end of the guide 121. At the light exit end of the guide, a tissue contact element 122 is arranged, for example a cylindrical rod of clear monocrystalline sapphire having an optically polished lateral face 122a, of the same diameter as the rod-shaped guide 121 and forming its continuation. The end of the tissue contact element 122 away from the guide 121 forms a contact surface 122c, highly polished and free from scratches. The anterior edge of the tissue contact element is rounded so as not to cut into the tissue.

In the known case, the tissue contact element is to be as thin a platelet as possible, intended merely to form a low-adhesion tissue contact surface. In the present case, the tissue contact element has the additional function of preventing excessive heating of the surface of a tissue to which the tissue contact surface 122c is applied. This is accomplished, in the coagulator of FIG. 4, in that the tissue contact element 122 has a comparatively great length L and an adequate cross section. The length L is preferably greater than 3 to 4 mm, preferably at least 6 mm, in particular 10 mm and over. The tissue contact element may be between 4 and 10 mm in diameter. To destroy deeper tissue using a lamp 114 with a rating of for example 150 W and an optical guide 121 about 10 to 20 cm in length, about 6 mm is an appropriate value for the diameter.

The tissue contact element, by virtue of its dimensioning, has so high a heat capacity that in one treatment cycle, normally requiring about 2 seconds, it will not heat so intensively as to alter the tissue surface in any undesirable manner. The temperature rise at the tissue contact surface 122c during a period of treatment of 2 seconds should expediently be at most 50 degrees, preferably at most 30 degrees, better yet at most 20 degrees Celsius, when the coagulator is to be used to destroy deep-lying blood vessels.

With radiation in the wavelength band from 0.6 to 1.4μ, substantially absorbed in the interior of the tissue only, the distribution of temperature t as a function of the depth of penetration d will be as shown by the curve 127 in FIG. 4a. In a region 129 in the interior of the tissue, the temperature will rise during the period of irradiation of for example 15 seconds so far that coagulation and destruction of tissue will take place in that location, in other words for example to temperature up to about 80° or 90° C. In a region adjoining the contact surface 122c down to a depth $d_1$, the temperature required for coagulation will not be attained, owing to the cooling effect of the contact element 122 applied to the tissue. From a depth $d_2$ onward, the radiation will have been attenuated to such an extent that the temperature of coagulation will fail to be reached likewise.

Much like that of FIG. 4, the radiation coagulator of FIG. 5 contains a tungsten-halogen incandescent lamp 214, a reflector 212, an optical guide rod 221 and a tissue contact element 222. Between the lamp 214 and the entrance end of the optical guide rod 221 there is an optical filter 215 in the form of a cell containing an aqueous solution of a red dye. An expedient alternative is a dielectric thin-layer filter having a suitable transmission characteristic. The filter 215 absorbs the shortwave components of radiation including ultraviolet radiation and the longer-wave infrared, so that substantially only radiation in the wavelength range between 0.6 and 1.4μ will enter the guide. The contact element 218 is closely adjacent to the light exit end of the guide rod 221 and is enclosed by a cooling means 230, which may be a finned cooling element, similar to those used for transistors, of a liquid-filled cell, optionally provided with cooling fins 230a in addition.

An alternative to the cooling system 230 in FIG. 5 is represented in FIG. 6. Here the tissue contact element 322 consists of a comparatively large disc, of which only a central portion 322' is traversed by the radiation S. Thus, coagulation takes place near the central portion only. The outer portion around the central portion 322' serves as a cooling element or heat sink. The radiation can be limited to the central portion 322' by an optical guide 321 in the shape of a truncated cone, its peripheral surface 321a being polished. For the tissue contact elements 222 and 322, preferably a material of high heat conductivity is employed, such as beryllium oxide. Suitable parts of beryllium oxide may be produced at comparatively moderate cost by hot pressing and sintering for example; they are sufficiently transparent to serve the present purpose.

FIG. 7 shows a light output system having an optical guide rod 422 serving simultaneously as tissue contact element. It has a truncated cone end 422d, forming a tissue contact surface 422c. The element 422 consists of a crystalline, transparent material of the above mentioned kind, having a high heat conductivity, so that the element 422 diverts heat from the tissue 429 adjacent to the tissue contact surface 422c acting as light exit surface. If use is made of unfiltered radiation from a 150-watt tungsten-halogen lamp operated at a color temperature of approx. 3000 K, a rod 422 50 mm in length, at least 10 mm in length, of sapphire monocrystal with a tissue contact surface 422c approx. 2 to 6 mm in diameter, a coagulation zone 429a penetrating deep into the tissue 429 can be produced. The resulting distribution of temperature as a function of the distance d from the tissue surface (skin) corresponds to the curve drawn solid in the graph of FIG. 7a. The tissue temperature at the tissue surface is limited, owing to withdrawal of heat by the rod 422 acting as a cooling element, to a moderate value $T_2$, higher than the coagulation temperature $T_3$ indeed, but not so high that carbonization, or an excessive adhesion of the tissue to the light exit surface 422c results. The removal of heat compensates to a certain extent for the intensity drop of the radiation entering the tissue, so that up to a considerable depth, a comparatively flat temperature distribution and a temperature above the coagulation temperature $T_3$ are obtained. When a tissue contact element of a poor heat conductor such as quartz glass or synthetic material is used, a temperature distribution corresponding to the dotted curve is obtained, in which case a very high temperature $T_1$ occurs at the tissue surface after only a short time. The tissue then chars at the surface, impeding any deeper penetration of the radiation, so that the hemorrhage is arrested less effectively and the tissue tends to adhere to the contact surface. Similar effects arise also when too thin a contact element of sapphire or the like is used.

The electric power input from the incandescent lamp serving as source of radiation should generally be at least 75 watts, preferably at least 100 watts. For satisfactory coagulation, generally an output density of at least 10 W/cm$^2$ or more is required in the cross section of the tissue contact element traversed by the radiation at the contact surface. The output density should preferably be at most 100 W/cm$^2$, so that no excessively rapid heating of the tissue will occur at the contact surface, with the danger that the tissue will dry out too rapidly at the contact surface and then adhere in an undesirable manner.

We claim:

1. In a radiation coagulation apparatus for applying radiation to a limited area of living tissue by direct contact of said apparatus therewith, said coagulation apparatus comprising an incandescent electric filament as a source of heat radiation, a housing enclosing said electric filament, and a radiation exit system including a tissue contact element of a crystalline dielectric material transmissive to the radiation forming a contact surface to be applied against said body tissue through which said radiation traverses, the improvement wherein
    said tissue contact element is comprised of sapphire, and has a radiation entrance surface facing said electric filament, and has an average thickness of at least 4 mm measured between the radiation entrance surface and the tissue contact surface in the direction of the radiation; and
    the radiation output density of said radiation source at the tissue contact surface of said contact element is at most 150 watts/cm$^2$.

2. A radiation coagulator according to claim 1, wherein the specific heat capacity and thermal conductivity of said radiation exit system each have a relatively high value such that the temperature at the contact surface of said contact element, while adjacent to body tissue and traversed by the radiation from the heat radiation source, will increase at most 50° C. with 2 seconds.

3. A radiation coagulator according to claim 1 or 2, wherein the tissue contact element has a relatively smooth surface and wherein the edges that can come into contact with body tissue are rounded.

4. A radiation coagulator according to claim 1 or 2 further including a heat sink, and wherein the side of a portion of said tissue contact element traversed by the radiation is in good heat-conductive communication with said heat sink.

5. A radiation coagulator according to claim 1, wherein the tissue contact element, at least adjacent to the radiation entrance surface facing said electric filament, is round in cross section with a diameter of at least 4 mm and is at least 6 mm in length in the direction of the radiation through the contact element.

6. A radiation coagulator according to claim 1, wherein the source of heat radiation is an electric incandescent lamp and wherein the region of said contact element adjoining said radiation source is cylindrical for at least 5 mm in length in the direction of the radiation.

7. A radiation coagulator according to claim 6, wherein the incandescent filament is substantially surrounded by an envelope, and the radiation entrance surface of said contact element is spaced apart from, but at most 10 mm distant from, the envelope of the incandescent filament.

8. A radiation coagulator according to claim 7, wherein the tissue contact element is at least 10 mm in length.

9. A radiation coagulator according to claim 8, wherein the contact element comprises a tip of diminishing cross section away from the source of radiation.

10. A radiation coagulator according to claim 9, wherein the diminishing tip is wedge-shaped.

11. A radiation coagulator according to claim 7, wherein the housing enclosing said incandescent filament includes a subtantially ellipsoidal reflector at a radial distance of at most 5 mm from said incandescent filament.

12. A radiation coagulator according to claim 6, wherein the lamp has a rating of 150 W and the diameter of the cylindrical region of said contact element is 12 mm.

13. A radiation coagulator according to claim 6, wherein the lamp has a rating of 250 W and the diameter of the cylindrical region of said contact element is 16 mm.

14. A radiation coagulator according to claim 6, wherein the lamp has a rating of 400 W and the diameter of the cylindrical region of said contact element is 25 mm.

15. A radiation coagulator according to claim 1, wherein the tissue contact element is a monocrystal.

16. A radiation coagulator according to claim 1, wherein the tissue contact element contains a material imparting an increased absorption thereto in the green and blue band of the spectrum.

17. A radiation coagulator according to claim 1, wherein an optical filter having a pass band from about 0.6$\mu$ to about 1.4$\mu$ is arranged between the source of radiation and the tissue contact element.

18. A radiation coagulator according to claim 1, wherein the source of radiation is an incandescent lamp having an electric power rating of at least 100 W.

19. A radiation coagulator according to claim 1, wherein the output density of the incoherent radiation is at least 10 watts per square centimeter at the contact surface.

20. A radiation coagulator according to claim 1, wherein the output density is at most 100 watts/cm$^2$.

21. A radiation coagulator according to claim 1, wherein the tissue contact element has a disc shape and is optically polished on its circumferential surface.

22. A radiation coagulator according to claim 1 further including a generally cylindrical tube member which encircles the tissue contact element, to thereby reduce glare.

23. A radiation coagulator according to claim 1 wherein said housing comprises a generally cylindrical tube.

24. A radiation coagulator according to claim 23, wherein said tube is generally straight.

25. A radiation coagulator according to claim 23, wherein said tube has a bend of about 45° in its middle.

26. A radiation coagulator according to claim 23, wherein said tissue contact element is mounted at the end of the tube so that the radiation path is generally coaxial with the cylindrical tube's axis.

* * * * *